(12) United States Patent
Nozawa

(10) Patent No.: US 7,241,013 B2
(45) Date of Patent: Jul. 10, 2007

(54) OPTOMETRIC APPARATUS

(75) Inventor: Noritsugu Nozawa, Toyokawa (JP)

(73) Assignee: Nidek Co., Ltd., Aichi (JP)

( * ) Notice: Subject to any disclaimer, the term of this patent is extended or adjusted under 35 U.S.C. 154(b) by 648 days.

(21) Appl. No.: 10/831,315

(22) Filed: Apr. 26, 2004

(65) Prior Publication Data

US 2004/0218146 A1    Nov. 4, 2004

(30) Foreign Application Priority Data

May 1, 2003   (JP)   ............................. 2003-126531

(51) Int. Cl.
*A61B 3/02* (2006.01)

(52) U.S. Cl. .................. 351/222; 351/217; 351/235

(58) Field of Classification Search ............. 351/222, 351/211, 212, 206, 205, 246, 247, 239, 237, 351/244

See application file for complete search history.

(56) References Cited

U.S. PATENT DOCUMENTS 5,281,984 A * 1/1994 Burton et al. ............... 351/221
5,929,971 A * 7/1999 Hosoi et al. ................ 351/237

FOREIGN PATENT DOCUMENTS

JP       A 9-276218       10/1997

* cited by examiner

*Primary Examiner*—Ricky Mack
*Assistant Examiner*—Tuyen Tra
(74) *Attorney, Agent, or Firm*—Oliff & Berridge, PLC

(57) ABSTRACT

An optometric apparatus comprises: a pair of right and left lens chamber units, each unit including a test window and optical elements to be selectively disposed in the test window; and a controller including a transmitting part which transmits a control signal in the form of an optical signal to the lens chamber units to selectively dispose the optical elements in the test window, the transmitting part being adapted to widen an extent of diffusion of luminous flux of the optical signal more greatly in a forward to upward directions than in a lateral direction.

7 Claims, 10 Drawing Sheets

OPTOMETRIC APPARATUS

BACKGROUND OF THE INVENTION

1. Field of the Invention

The present invention relates to an optometric apparatus for subjectively examining (measuring) a refractive power of an eye of an examinee.

2. Description of Related Art

There has been known an optometric apparatus constructed to subjectively examine (measure) a refractive power (a visual acuity) of an eye of an examinee by presenting optotypes forward of the eye through an optical element such as a spherical lens and cylindrical lens placed in front of the eye. In this optometric apparatus, a plurality of lens disks, each holding various optical elements are rotatably placed in each housing of a right and left lens chamber units each having a test window. Each lens disk is rotated by a motor to selectively dispose the optical elements into the test window. Some optometric apparatuses of this type include a wireless controller which transmits a control signal in the form of an optical signal to the motor and others associated with the lens chamber units.

SUMMARY OF THE INVENTION

The present invention has been made in view of the above circumstances and has an object to overcome the above problems and to provide an optometric apparatus provided with a wireless controller with high operationality.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optometric apparatus comprising: a pair of right and left lens chamber units, each unit including a test window and optical elements to be selectively disposed in the test window; and a controller including a transmitting part which transmits a control signal in the form of an optical signal to the lens chamber units to selectively dispose the optical elements in the test window, the transmitting part being adapted to widen an extent of diffusion of luminous flux of the optical signal more greatly in a forward to upward directions than in a lateral direction.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
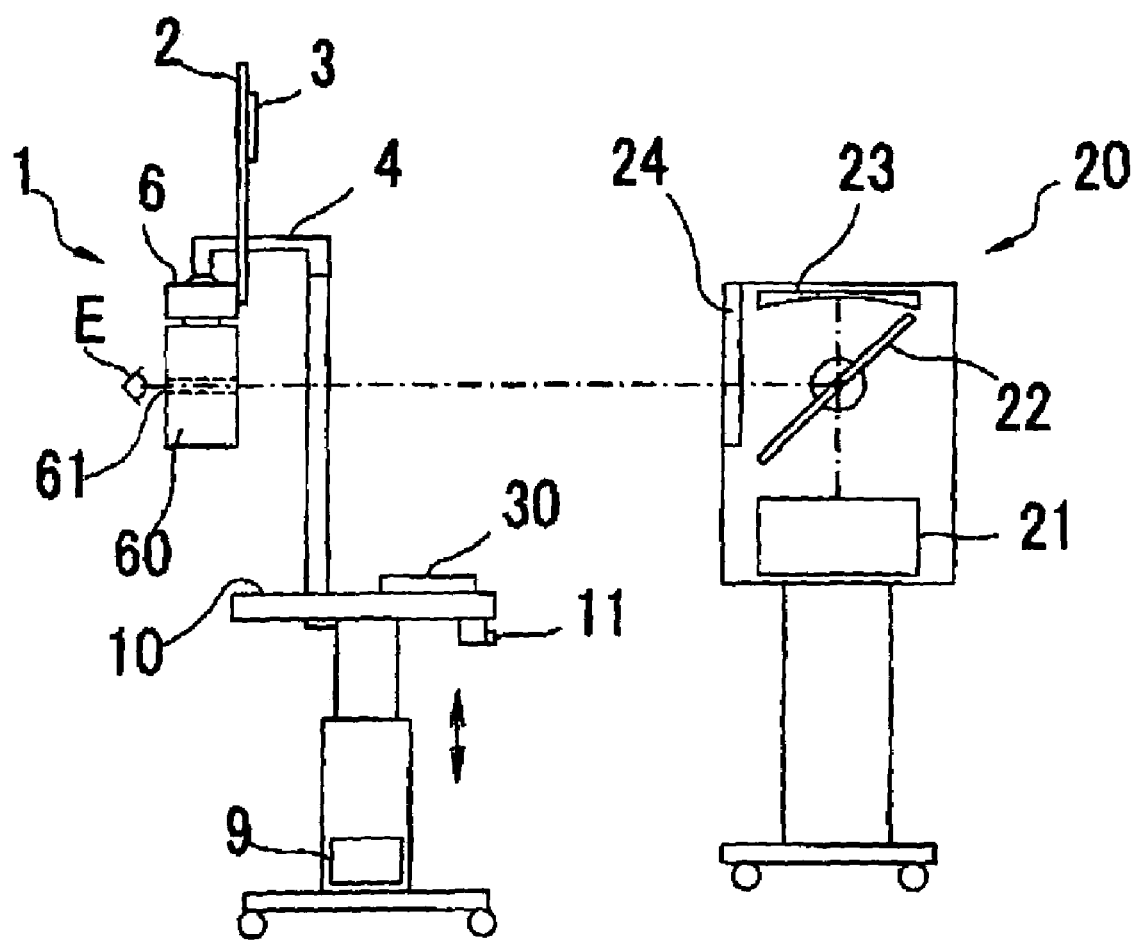
FIG. 1 is a schematic structural view of an optometric system including an optometric apparatus in a preferred embodiment.
Figure 2:
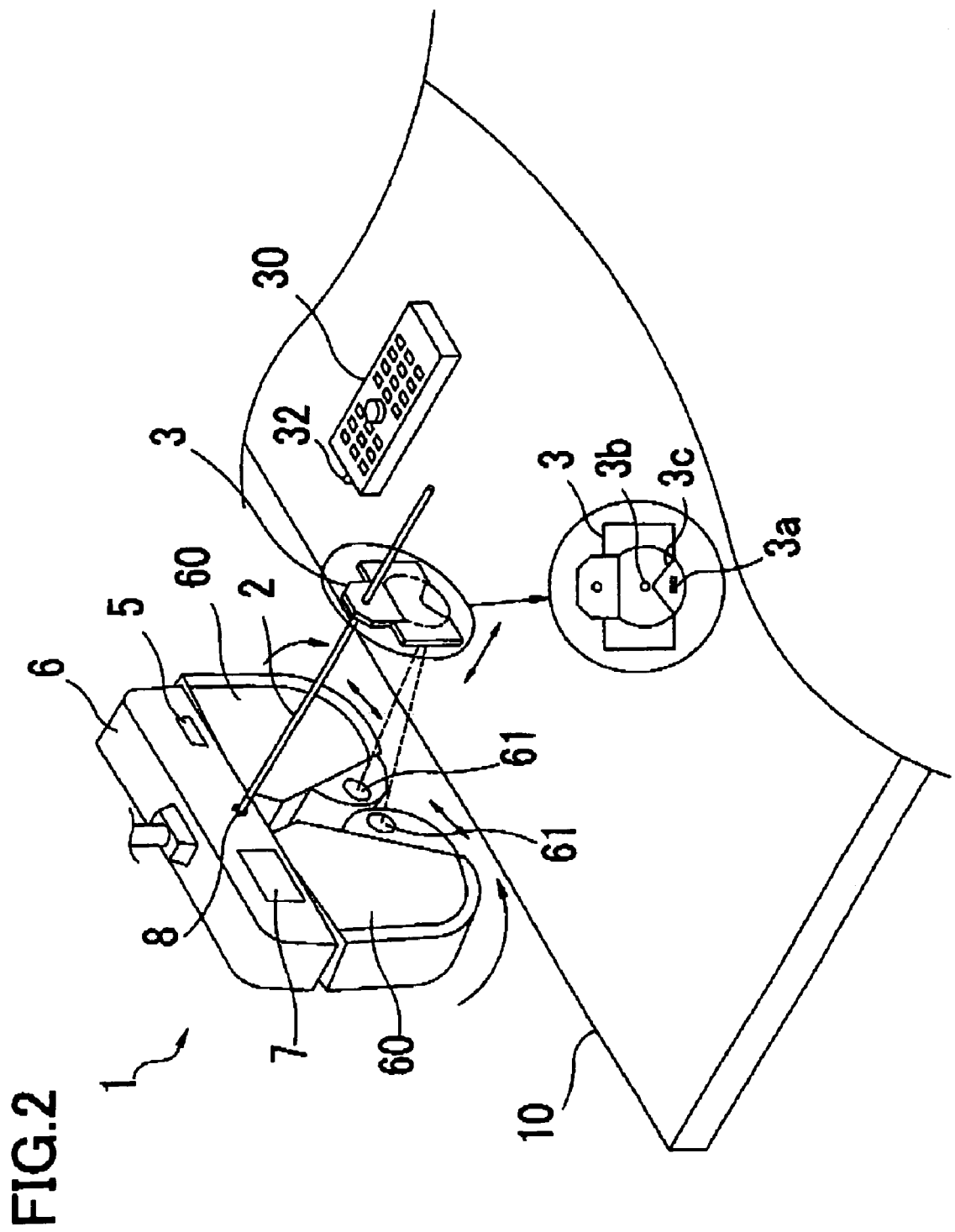
FIG. 2 is a schematic structural view of the optometric apparatus.
Figure 3:
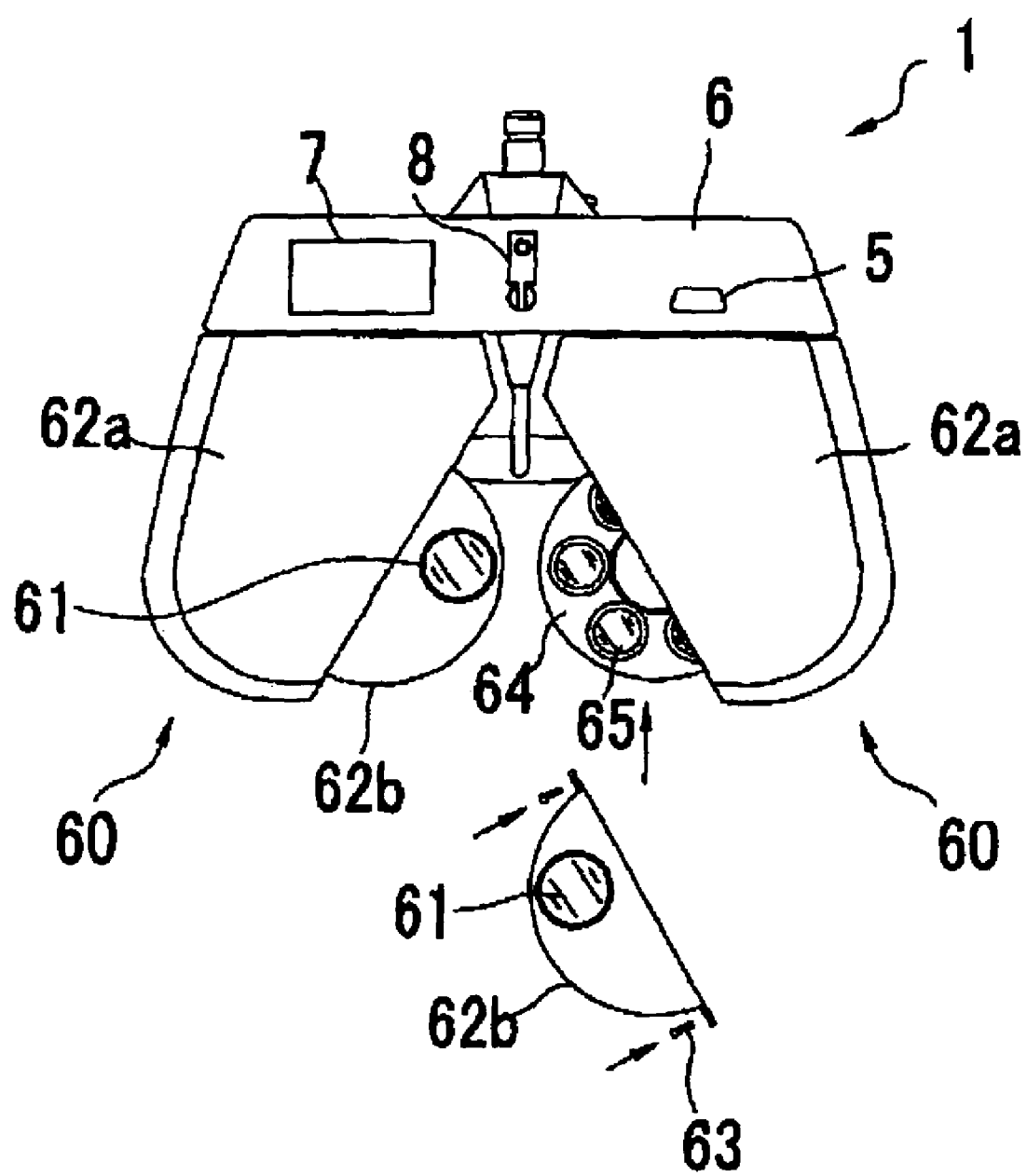
FIG. 3 is a schematic structural view of the optometric apparatus.

A detailed description of a preferred embodiment of the present invention will now be given referring to the accompanying drawings. FIG. 1 is a schematic structural view of an optometric system including an optometric apparatus in the present embodiment. FIGS. 2 and 3 are schematic structural views of the optometric apparatus seen from an operator side.

A main unit 1 of the optometric apparatus includes a pair of right and left lens chamber units 60 having symmetric shapes, each having a test window 61, and a movement unit 6 supporting (holding) the lens chamber units 60 in a hanging state. The movement unit 6 houses a movement mechanism 40 (see FIG. 5) including a slide mechanism for adjusting the interval between the right and left lens chamber units 60 and a convergence mechanism for adjusting a convergence angle (an inward directing angle) of the lens chamber units 60.

The main unit 1 is supported above a table 10 by a support arm 4 provided on the table 10. By operation of a switch 11 for vertical movement, unillustrated driving means is driven to vertically move the table 10 to adjust the height of the top plate of the table 10, namely, the height of the main unit 1.

An optotype presenting device 20 to be used for a far vision examination is placed at a predetermined distance (e.g., 1 m) from the main unit 1 (FIG. 1 schematically shows the inner structure of this device 20). The device 20 internally includes an optotype presenting part 21 for presenting various examination optotypes, a beam splitter 22, a concave mirror 23, and others. The light of the optotype from the presenting part 21 passes through the beam splitter 22 and is reflected by the mirror 23. The optotype light reflected by the mirror 23 is reflected by the beam splitter 22 toward an examinee's eye E through a window 24.

A rod 2 is connected to an attachment member 8 provided in the movement unit 6. On the rod 2, an optotype presenting unit 3 for use in a near vision examination is mounted movably (slidably) in the axial (longitudinal) direction of the rod 2. This unit 3 includes a chart 3a for the near vision examination on which a plurality of examination optotypes are drawn or printed. The near vision chart 3a is rotatable about an axis 3b of the presenting unit 3. By rotation of this chart 3a, a desired one of the optotypes is presented in a presenting window 3c. The presenting unit 3 is hung on the rod 2 so that the height of the chart 3a to be presented in the presenting window 3c is the same as the height of the test window 61. The rod 2 is graduated to show a distance (a distance for the near vision examination distance, hereafter, a near-vision distance) from the eye E positioned in front of the test window 61 to the chart 3a. Thus, in the near vision examination, the chart 3a can be disposed in advance at a desired distance from the eye E. The attachment member 8 is constructed to flip up the rod 2 connected thereto. Accordingly, the rod 2 can be held in a flipped-up position as shown in FIG. 1 except during the near vision examination.

A controller 30 includes switches for operating the main unit 1 and the optotype presenting device 20 and switches for automatically or manually performing the far vision examination and the near vision examination. The controller 30 will be mentioned in detail later.

A signal receiving part 5 is provided in the main unit 1 to receive a control signal from the controller 30. This receiving part 5 includes a light receiving element (photoreceptor) sensitive to infrared light. A liquid crystal display (LCD) 7 is used to display information on the control signal from the controller 30 (for example, data on spherical power, cylinder power, and others of an optical element 65 to be disposed in the test window 61 and data on an optotype to be presented). A relay unit 9 is built in the table 10 and linked to the optotype presenting device 20 and others. This relay unit 9 is used to transmit the control signal which the main unit 1 receives from the controller 30, to the optotype presenting device 20 and others as required.

In a housing of each lens chamber unit 6, a plurality of lens disks 64 are rotatably placed, on each of which many various optical elements (lenses and the like) 65 are mounted (held) in a circumferential arrangement. Each lens disk 64 is rotated by operation of the controller 30 to selectively dispose one of the optical elements 65 into the test window 61. As shown in FIG. 3, the housing of each lens chamber unit 60 includes a main cover 62a and a disk cover 62b. When the disk cover 62b is detached from the main cover 62a, a part (about half) of the circumferential edge of each lens disk 64 placed in the housing is exposed. At this time, only the part of each lens disk 64 is exposed from the main cover 62a, and other mechanisms and electric systems remain covered, not exposed.

Figure 4:
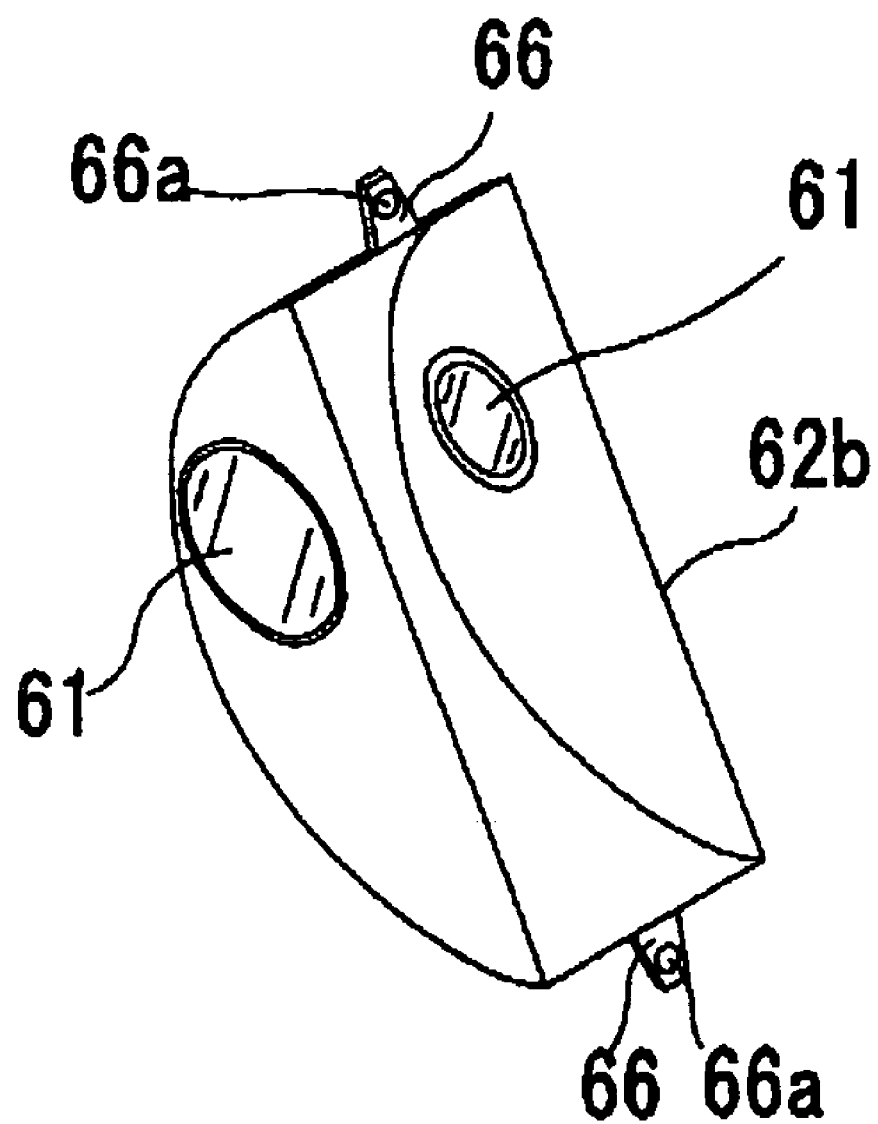
FIG. 4 is a schematic structural view of a disk cover.

As shown in FIG. 4, the disk cover 62b is of a semicircular shape in front view (see FIG. 3) and has an inner cavity. This disk cover 62b is provided with the test windows 61 in semicircular front and rear faces which will face an examinee and an examiner respectively. The disk cover 62b is further provided, at upper and lower ends, with attaching members 66 each having a hole 66a which a screw 63 serving as attachment means passes through. Correspondingly, the main cover 62a is provided with female screw portions not shown for attachment of the disk cover 62b. To attach the disk cover 62b to the main cover 62a, the screws 63 passing through the holes 66a of the attaching members 66 are tightened into the female screw portions. To detach the disk cover 62b from the main cover 62a, on the other hand, the screws 63 are simply loosen and taken off from the female screw portions. In this manner, the disk cover 62b can easily be attached and detached.

When the disk cover 62b is detached, the inside of each test window 61 can easily be cleaned. It is also possible to easily clean the optical elements 65 mounted in each lens disk 64. Because each lens disk 64 can be rotated manually by a person (for example, an examiner) who holds the exposed portion thereof, all of the optical elements 65 are allowed to be cleaned. Each lens disk 64 has an opening with no lens.

In the present embodiment, the disk cover 62b provided with the test windows 61 is adapted to be detachably attached. Instead thereof, a structure that only the test windows 61 are detachably attached may be adopted. This structure that only the test windows 61 are detachably attached is realized, for example, in such a manner that a holder which holds transparent members such as glass and plastic resin forming the test windows 61 is screwed or mounted by click mechanism in the housing of each lens chamber unit 60. With this structure, the test windows 61 can be attached and detached together with the holder. In this case, a dial switch 31b (see FIG. 6) on the controller 30 is operated to bring the optical elements 65 mounted in each lens disk 64, one by one, to a position where the test window 61 has been detached so that all of the optical elements 65 can be cleaned in turn.

In many cases, dirt on the inside of each test window 61 is caused when moisture including dust and oil content evaporated due to increased temperature of the inside of the main unit 1 by heating of a motor adheres to and condenses on the test window 61 exposed to outside air, resulting in residual dew condenses or dried marks thereof. To prevent the generation of the dew condenses, the test window is preferably structured as a double-layer test window which serves as a heat insulating layer or a test window provided with heating wire.

Figure 5:
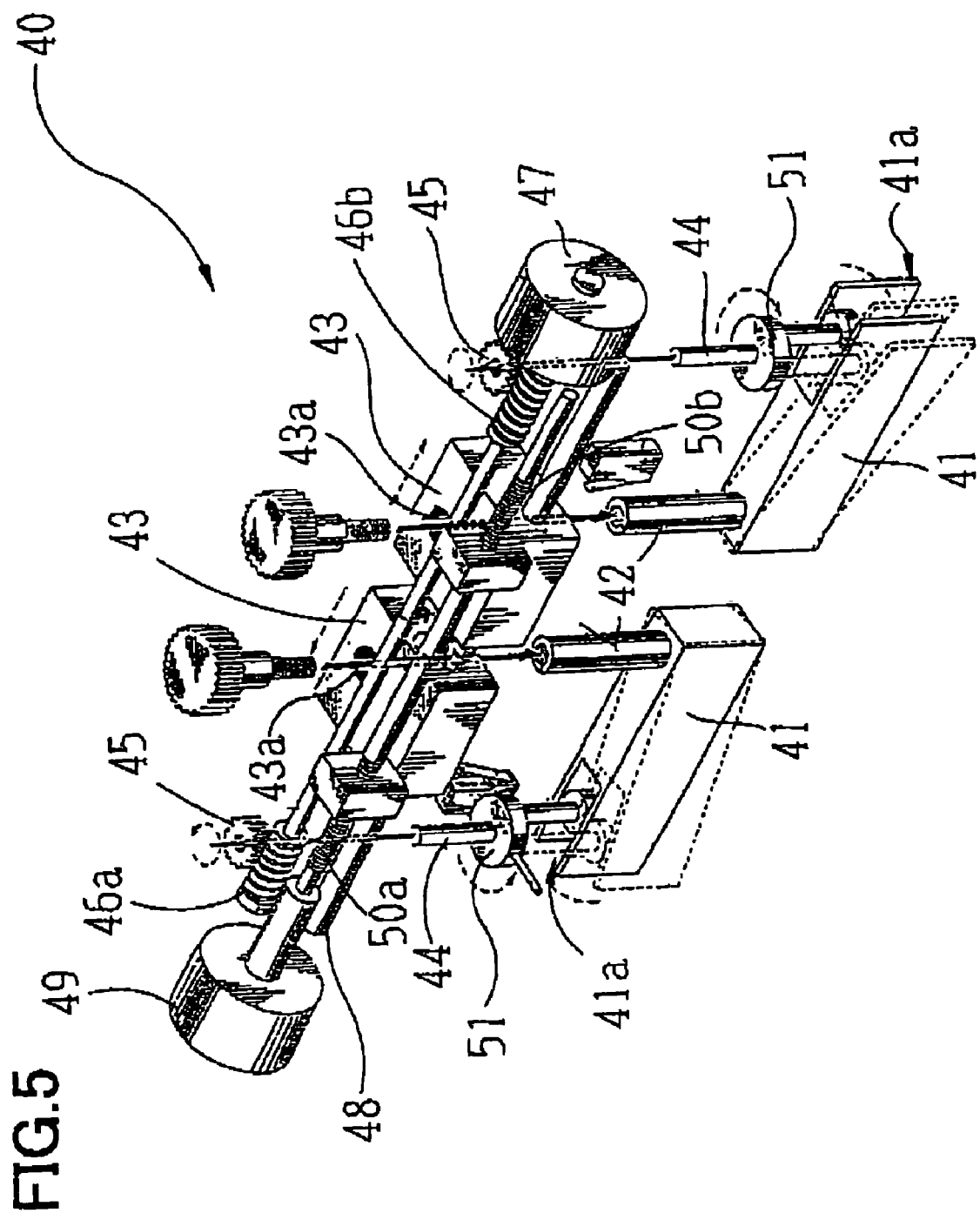
FIG. 5 is a schematic structural view of a moving mechanism of the optometric apparatus.

The movement mechanism 40 is explained below with reference to FIG. 5. Shafts 42 fixed to hanging plates 41 which hang the lens chamber units 60 respectively are rotatably engaged in holes 43a of slidable bases 43. Shafts 44 for slanting the hanging plates 41 in an inward direction are connected to worms 46a and 46b respectively through gears 46. At one end (lower end in FIG. 5) of each of the shafts 44, an eccentric shaft 51 is attached. The tip end portion of the eccentric shaft 51 is engaged in a groove 41a formed in the hanging plate 41a. The worms 46a and 46b are connected to driving means including a pulse motor 47, and will be rotated by rotation of the motor 47. The rotation of the worms 46a and 46b causes the eccentric shafts 51 to rotate by way of the gears 45 and the shafts 44, thereby converging the hanging plates 41. The slidable bases 43 are movable (slidable) on a fixed guide 48 in its axial direction. Driving means including a pulse motor 49 and the fixed guide 48 are secured to a fixed bracket not shown. Screws 50a and 50b having threading directions opposite to each other are connected to the motor 49 and are engaged with female screws of the slidable bases 43. When the motor 49 is rotated, accordingly, the two slidable bases 43 are moved (slid) in opposite directions. By means of the movement mechanism 40 having the above structure, an interval and a convergence angle between the right and left lens chamber units 60 (the right and left test windows 61) are adjusted.

Figure 6:
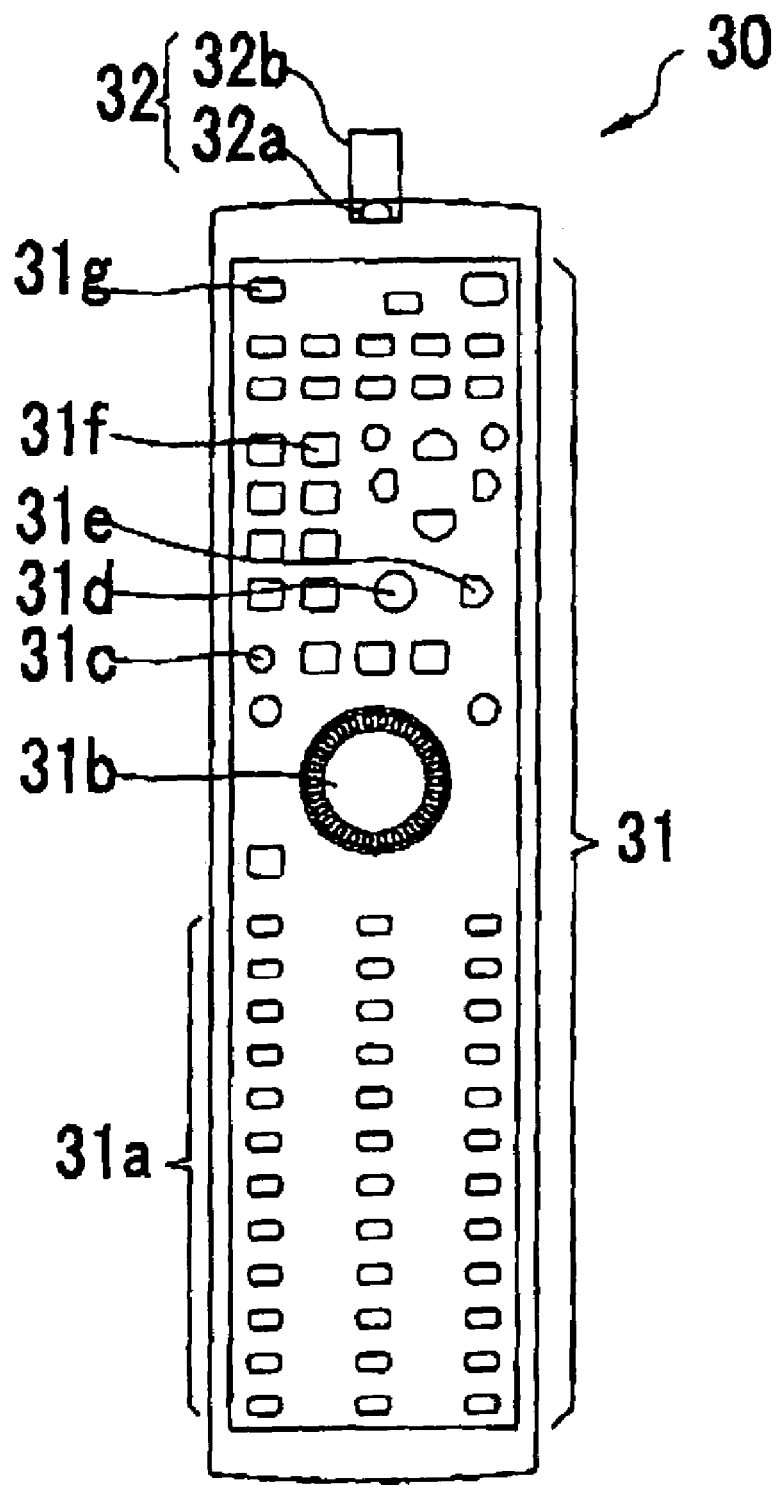
FIG. 6 is a schematic structural view of a controller.

Referring to FIG. 6, the controller 30 is explained below. This controller 30 is of a shape and size allowing an examiner to handle by one hand. The controller 30 includes a switch part 31 for various operations. This switch part 31 includes an optotype switch group 31a for selecting a desired optotype from a plurality of optotype groups, the dial switch 31b for selecting various functions, inputting numerals, and disposing the optical element 65 satisfying examination conditions (spherical power, cylinder power, axis, etc.) into the test window 61, an input switch 31c for inputting data on objective measurement results, a start switch 31d for starting a programmed eye-examination (optometry), a program advance switch 31e, a PD switch 31d for setting (inputting) a pupillary distance (PD), and a menu switch 31g for setting various examination conditions. In the present optometric apparatus, the PD can be set in 1 mm steps in a range of 48 mm to 80 mm.

In the top of the controller 30, there is provided a signal transmitting part 32 including a light emission part 32a including an LED which emits infrared light to be used for a control signal and a diffusion part 32b attached just ahead of the light emission part 32a. The diffusion part 32b serves to widely diffuse the control signal emitted from the light emission part 32a so that the outgoing direction of the signal is greatly extended from forward to upward.

Figure 7A:
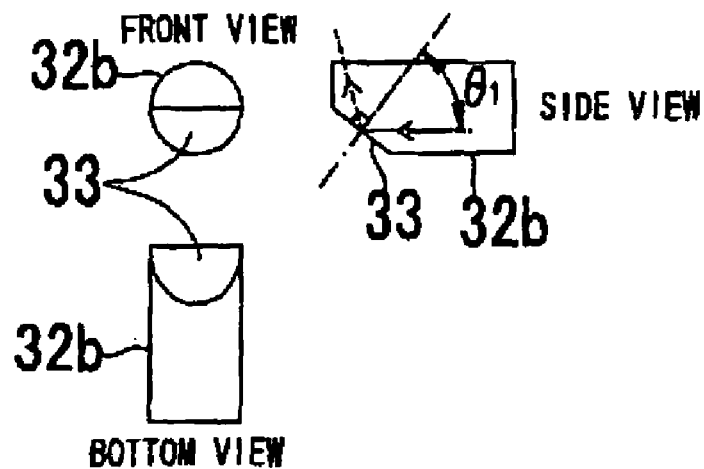
FIG. 7A shows a diffusion part in front, right side, and bottom views.
Figure 7B:
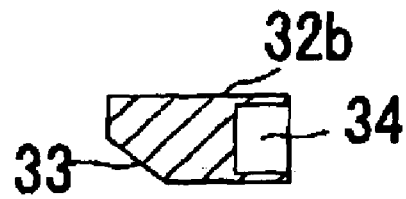
FIG. 7B is a sectional side view of the diffusion part.
Figure 7C:
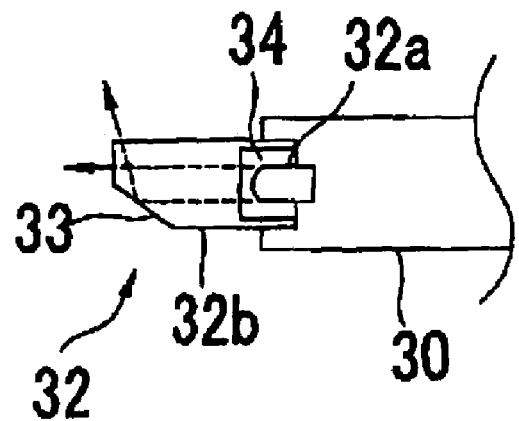
FIG. 7C is a schematic side view of a signal transmitting part.

FIG. 7 are schematic structural views of the transmitting part 32; specifically, FIG. 7A shows the diffusion part 32b in front, right side, and bottom views; FIG. 7B is a sectional side view of the diffusion part 32b; and FIG. 7C is a schematic side view of the transmitting part 32.

The diffusion part 32b is an optical member of a substantially cylindrical shape, made of a transparent resin such as acrylate resin. This diffusion part 32b has an end cut out in half circular face at a slant, forming a beveled face 33. This beveled face 33 is formed at a slant angle determined so that an incident angle $\theta_1$ of luminous flux (optical signal) from a horizontal direction onto the beveled face 33 is a critical angle or more in order to totally reflect the luminous flux. Furthermore, the beveled face 33 is also configured to have the slant angle of 45° or less with respect to the center axis (in a longitudinal direction) of the diffusion part 32b so that the luminous flux is turned upward and then goes forward.

The diffusion part 32b in the present embodiment is made of acrylate resin with a reflective index of 1.49. When the luminous flux passes from this acrylate resin into air, an incident angle $\theta_1$ of the luminous flux becomes the critical angle at approx. 42.15°. Accordingly, to provide an incident angle $\theta_1$ larger than the critical angle and allow the luminous flux turned (reflected) upward to go forward, the slant angle of the beveled face 33 is set at 35° (the incident angle $\theta_1$, 55°).

In the present embodiment, the incident angle $\theta_1$ to the beveled face 33 is set to be larger than the critical angle in order to totally reflect the luminous flux from the horizontal direction, but it is not limited thereto.

For instance, the beveled face 33 may be applied with a coating having a property of totally reflecting infrared light or partially reflecting infrared light at a predetermined ratio.

The controller 30 is formed at its top with a recess not shown in which the diffusion part 32b is mounted, and the light emission part 32a is centrally placed in the recess. As shown in FIG. 7B, the diffusion part 32b is formed at its bottom with a recess 34 having a predetermined depth in the axial direction of the diffusion part 32b. This recess 34 serves to internally hold the light emission part 32a when the diffusion part 32b is mounted in the recess of the controller 30. With this structure, the diffusion part 32b is easily detachably mounted in the controller 30.

The diffusion part 32b is mounted in the controller 30 so that the beveled face 33 is oriented downward. When infrared light for the control signal is emitted from the light emission part 32a of the controller 30 in which the diffusion part 32b has been mounted, an upper portion of the emitted luminous flux travels in straight lines through and then directly exits the diffusion part 32b in a forward direction. A lower portion of the emitted luminous flux similarly travels in straight lines through the diffusion part 32b and then totally or partially reflected at the beveled face 33 to go upward.

Figure 10A:
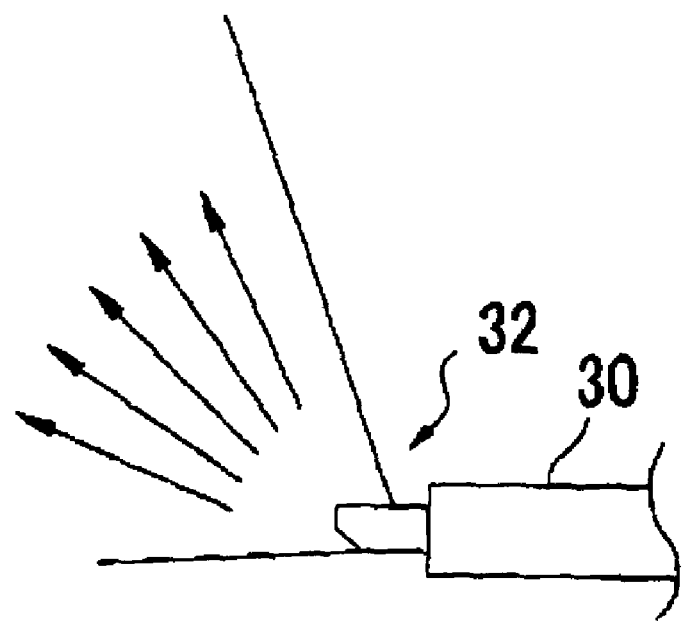
FIG. 10 is a view showing a diffused state of a control signal by a diffusing part.
Figure 10B:
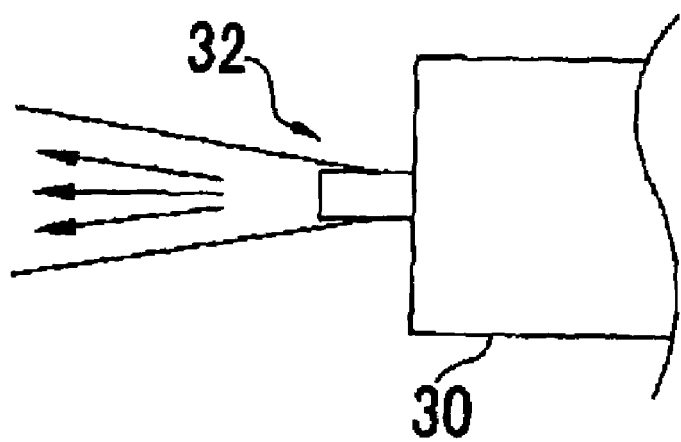

FIG. 10 are views showing a diffused state of the infrared luminous flux for the control signal from the transmitting part 32. As shown in FIG. 10A, the extent of diffusion of the luminous flux in forward to upward directions is greater than that in the case where the diffusion part 32 is not mounted in the controller 30. As shown in FIG. 10B, on the other hand, the extent of diffusion of the luminous flux in a lateral direction is substantially the same as in the case where the diffusion part 32 is not mounted in the controller 30.

As above, the luminous flux is not diffused in all directions but is diffused only vertically from the forward direction to the upward direction. This makes it possible to allow the receiving part 5 provided in the main unit 1 positioned above the controller 30 to receive the control signal from the controller 30 disposed on the table 10 as shown in FIG. 2 while keeping a reduction in light intensity to the minimum. Consequently, there is no need for the examiner to operate the controller 30 while pointing it at the receiving part 5. Accordingly, operationality and convenience of the controller 30 can be enhanced. When the orientation of the diffusion part 32, which is rotatably mounted, is changed, the traveling direction of the infrared light for a control signal can be changed correspondingly.

The emission part 34 may include a plurality of LEDs having different placement angles. Further, just ahead of the emission part 34, there may be placed an optical member capable of deflecting luminous flux, such as a cylindrical lens. In this case, the luminous flux can be diffused more widely from the frontward direction to the upward direction.

Figure 8:
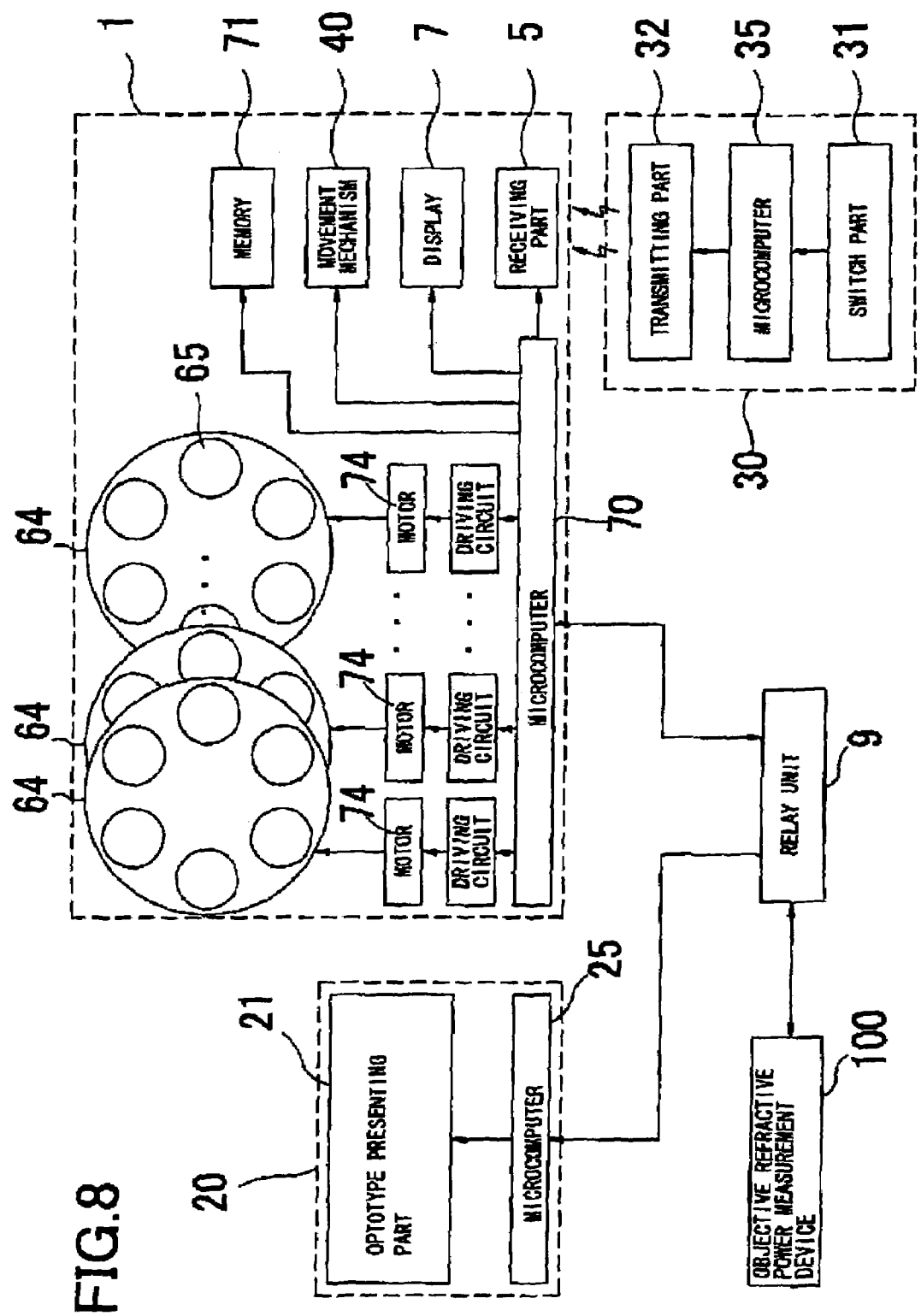
FIG. 8 is a schematic block view of a control system in the optometric system in the embodiment.

The operation of the optometric system having the above structure is described below with reference to a schematic block view of a control system shown in FIG. 8. Herein, a subjective examination (far vision and near vision examinations) is performed by use of an examination program determined in advance in relation to procedures of the subjective examination including the near vision examination.

It is to be noted that the optometric apparatus used in the present embodiment has a structure that, if the examinee's PD is 54 mm or less in the near vision examination using the near-vision distance of 35 cm from the eye E to the near vision chart 3a, the right and left lens chamber units 60 when correspondingly moved closer and converged will come into contact with each other.

After having the examinee to sit down in front of the main unit 1, the examiner operates the switch 11 to adjust the height of the test window 61 to the height of the eye E. The examiner then operates the input switch 31c on the controller 30 for input (transfer) of objective examination data (spherical power, cylinder power, axis, pupillarly distance, etc.) into the main unit 1. On pressure of the input switch 31c, the microcomputer 35 in the controller 30 transmits a control signal from the transmitting part 32 for transfer of the objective examination data from an objective refractive power measurement device 100 to the main unit 1. The receiving part 5 in the main unit 1 receives the control signal transmitted from the transmitting part 32. In response to the control signal received by the receiving part 5, a microcomputer 70 in the main unit 1 obtains the objective examination data from the objective refractive power measurement device 100 by way of the relay unit 9 and stores the data in a memory 71.

Based on the PD data inputted, the microcomputer 70 drives the movement mechanism 40 to move (slide) the right and left lens chamber units 60 to adjust the interval between the lens chamber units 60 to the examinee's PD. Based on the other objective examination data, the microcomputer 70 also drives the pulse motor 74 to rotate each lens disk 64, thereby disposing appropriate ones of the optical elements 66 having a predetermined power (diopter) in the test window 61. Simultaneously, the test window 61 not to be used is shielded.

Then, the examiner pushes the start switch 31d on the controller 30 to start the examination program. Upon pressure of the switch 31d, the microcomputer 35 transmits the control signal from the transmitting part 32 to present an optotype corresponding to the examination steps of the examination program the optotype presenting device 20. The microcomputer 25 in the optotype presenting device 20 receives the control signal from the receiving part 5 via the relay unit 9 and, in accordance with this control signal, drives the optotype presenting part 21 to project an optotype light toward the eye E.

The examiner operates the program advance switch 31e to advance the examination program to sequentially perform a spherical power adjustment, an axis measurement, a cylinder power measurement, and others, thereby determining a correction power for far vision to each of the left and right eyes. When further advanced, the program goes into a near vision examination step. At this time, an examination mode of the apparatus is switched from a far vision examination mode to a near vision examination mode.

To execute the near vision examination, the examiner turns the rod 2 down from the flipped-up position to a horizontal position to place the optotype presenting unit 3 in front of the test window 61, i.e., the eye E as shown in FIG. 2. The examiner moves (slides) the unit 3 on the rod 2 in its axial direction to provide a near-vision distance (a presenting distance) necessary for the examinee. This near-vision distance has been determined in advance (35 cm in the present embodiment). To change the near-vision distance to 50 cm, 70 cm, or others, the examiner operates the menu switch 31g on the controller 30 to establish a near-vision distance changing mode and selects an appropriate near-vision distance with the dial switch 31b. To change the PD information, the examiner should operates the PD switch 31f to establish a PD changing mode and changes (sets) the PD information with the dial switch 31b. A screen for the above changes is displayed in the display 7 of the main unit 1. The near-vision distance in the optometric apparatus in the present embodiment can be selected in 5 cm steps in a range of 35 cm to 70 cm.

When receives the signal representing the switching to the near vision examination mode or thereafter the near-vision distance is selected with the controller 30, the microcomputer 70 drivingly controls the movement mechanism 40 based on the received near-vision distance information and PD information to converge and move (slide) the right and left lens chamber units 60. This driving-control of the movement mechanism 40 is performed by control of driving amounts (the number of pulses) of the pulse motors 47 and 49.

Specifically, the right and left lens chamber units 60 are converged and moved (slid) by changing a convergence angle to be appropriate for the PD of the examinee and the presenting distance (near-vision distance) of the near vision chart 8a and by moving the lens chamber units 60 closer to each other by a predetermined distance to narrow the interval between the right and left test windows 61 (hereinafter, referred to as "PD correction"). This PD correction is performed because the PD in the near vision examination becomes narrower than that in the far vision examination due to the convergence of the examinee's eyes.

Figure 9:
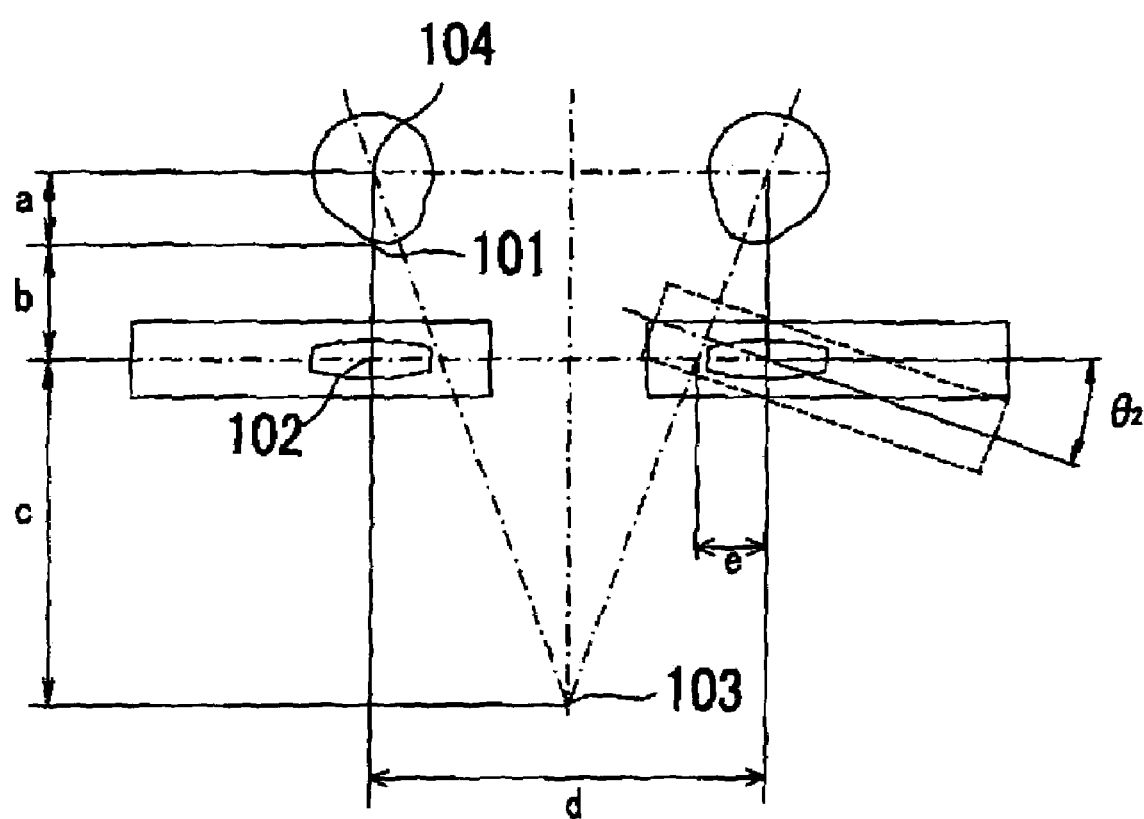
FIG. 9 is a view explaining a principle for determining a convergence angle and a PD correcting distance.

FIG. 9 is an explanatory view to show the principle for determining the convergence angle and the PD correcting distance according to the examinee's PD and the presenting distance (near-vision distance) of the near vision chart 3a. In FIG. 9, numeral 104 is a cycloduction point; 101, a corneal vertex point (in far vision); 102, a center of rotation of each shaft 42; and 103, a near-vision fixing point where the near vision chart 3a is placed. Assuming that each distance between the cycloduction point 104 and the near-vision fixing point 103 is a, b, and c, and the PD in far vision is d, a convergence angle $\theta_2$ of the lens chamber units 60 is expressed by the following expression (1):

$$\theta_2 = \tan^{-1}\frac{d}{2(a+b+c)} \quad (1)$$

Further, the PD correcting distance, e, in this stage is expressed by the following expression (2):

$$e = (a-b)\tan\theta_2 \quad (2)$$

Using the above expressions, the convergence angle and the PD correcting distance can be determined.

Based on the examinee's PD and the presenting distance (near-vision distance) of the near vision chart 3a, as above, the convergence and PD correction of the right and left lens chamber units 60 are performed to substantially align the visual axis of the eye E with the optical axis of the optical element 65 disposed in the test window 61 during the near vision examination.

In the case where the examinee's PD is narrow, however, the lens chamber units 60 are likely to contact with each other when the convergence and PD correction of the lens chamber units 60 are made so that the visual axis of the eye E matches the optical axis of the optical element 65 (hereinafter, referred to as "full convergence"). In the present embodiment, therefore, the optometric apparatus is adapted to perform the convergence and the PD correction in different manners between the case where the units 60 are likely to contact with each other and the other case where the units 60 are unlikely to contact with each other.

Table 1 shows the convergence and the PD correction of the lens chamber units 60 for each PD in the optometric apparatus with the near-vision distance of 35 cm. In Table 1, a "convergence angle (Full)" is a convergence angle needed to achieve full convergence and a "convergence angle (Actual)" is a convergence angle in the present embodiment. A "PD correcting distance (Full)" and a "PD correcting distance (Actual)" are also used similarly to the above "convergence angle (Full)" and others. A "PD correcting distance (Limit)" indicates a PD correcting distance limit to which the PD correction is allowed. The convergence angle and the PD correcting distance are calculated by rounding off the number to the first decimal place for convenience

TABLE 1

| PD (in far vision) | CA (Full) | CA (Actual) | PD CD (Full) | PD CD (Actual) | PD CD (Limit) | Presence/absence of contact due to full converging motion |
|---|---|---|---|---|---|---|
| 56 mm | 4.4° | 4.4° | 5.6 mm | 5.6 mm | — | Absence |
| 54 mm | 4.3° | 4.3° | 5.4 mm | 5.4 mm | — | Absence |
| 52 mm | 4.1° | 2.8° | 5.2 mm | 3.6 mm | 4.4 mm | Presence |
| 50 mm | 3.9° | 1.4° | 5.0 mm | 1.8 mm | 2.6 mm | Presence |
| 48 mm | 3.8° | 0° | 4.8 mm | 0 mm | 0 mm | Presence |

CA: convergence angle,
CD: correcting distance

As seen in Table 1, in the case where the near-vision distance was 35 cm and the examinee's PD (in the far vision examination) was 54 mm or more (54 mm to 80 mm), the lens chamber units 60 did not contact even when the full convergence was performed. To make the full convergence for the PD of 54 mm, for example, the convergence angle of the lens chamber units 60 needs be set at 4.3° and the PD correcting distance, at 5.4 mm. Because the contact will not be caused when the PD is 54 mm, for actual convergence of the lens chamber units 60, the convergence angle can be set at 4.3° and the PD correcting distance, at 5.4 mm.

In the case where the full convergence can be performed based on the near-vision distance and the examinee's PD set as above without causing the contact between the lens chamber units 60, these units 60 are converged and moved for the PD correction so that the visual axis of the eye E substantially matches the optical axis of the optical element 65.

On the other hand, in the case where the examinee's PD (in the far vision examination) is 54 mm or less, as shown in Table 1, the full convergence to substantially align the visual axis of the eye E with the optical axis of the optical element 65 results in the contact between the lens chamber units 60. In this case, the microcomputer 70 determines the convergence angle and the PD correcting distance in a range that will not cause the contact between the lens chamber units 60, even though the optical axis of the optical element 65 is not substantially aligned with the visual axis of the eye E, and then drives the movement mechanism 40 based on the determined settings. This makes it possible to reduce the prismatic effect caused by the optical element 65 to the minimum.

In the present embodiment, when the PD is 54 mm, the full convergence of the lens chamber units 60 can be achieved with the convergence angle of 4.3° and the PD correcting distance of 5.4 mm. When the PD is 48 mm, the driving of the lens chamber units 60 is disabled. Thus, the convergence angles and the PD correcting distances for target PDs (48 mm to 54 mm in the present embodiment), for which the driving of the lens chamber units 60 is enabled, are equally divided in that range and the convergence angle and the PD correcting distance for actually converging the lens chamber units 60 and moving them for the PD correction are determined.

For instance, to perform the full convergence for the examinee's PD of 52 mm, it is necessary to set the convergence angle of the lens chamber units 60 at 4.1° and the PD correcting distance at 5.2 mm as shown in Table 1. However, based on the convergence angle of 2.8° and the PD correcting distance of 3.6 mm, the lens chamber units 60 are actually converged and moved for the PD correction. For the examinee's PD of 50 mm, the convergence and the PD correction of the lens chamber units 60 are actually performed based on the convergence angle of 1.4° and the PD correcting distance of 1.8 mm. Those conditions have been stored in advance in the memory 71 so that the microcomputer 70 selectively determines an appropriate of the conditions from the memory 71 according to the inputted pupillary distance and near-vision distance.

In the present embodiment, the case where the near-vision distance is 35 cm is explained. In the other cases where the near-vision distance is not 35 cm, the same control of convergence and PD correction is similarly executed when the contact between the lens chamber units 60 is likely caused due to the examinee's PD.

In the present embodiment, the convergence angles and the PD correcting distances for the PDs of 48 mm to 54 mm are equally divided in that range and the convergence angle and PD correcting distance for actually converging the lens chamber units 60 and moving them for the PD correction are used, but they are not limited thereto. As shown in the "PD correcting distance (Limit)" in Table 1, for the PDs which are likely to cause the contact between the lens chamber units 60, the convergence angle limit and the PD correcting distance limit for each PD may be set and the convergence and the PD correction of the lens chamber units 60 may be performed based on those set values. In the case where the near-vision distance is 35 cm and the examinee's PD is 52 mm, for example, the convergence angle is set at 2.8° and the PD correcting distance is set at 4.4 mm which is a limit for this convergence angle and the convergence and PD correction of the lens chamber units 60 are performed.

The prismatic effect caused due to misalignment between the visual axis of the eye E and the optical axis of the optical element 65 can be reduced more largely by adjustment of the PD correcting distance rather than by adjustment of the convergence angle. Thus, the PD correcting distance may be determined at a limit or in preference to the convergence angle and adjusted.

After completion of the convergence and the PD correction of the lens chamber units 60, the examiner carries out the near vision examination on the examinee's right and left eyes respectively to check a spherical power and others. Under the above control, the convergence and the PD correction of the lens chamber units 60 are performed to a certain extent even in the case where the units 60 are likely to contact. Accordingly, the optometric apparatus according to the invention enables high-precision examination as compared with the conventional apparatus. After the near vision examination, upon pressure of a switch not shown on the controller 30, the examination data can be printed out. Based on a signal from this print switch, the examination program is terminated.

In the above embodiment, the explanation is made by using the examination program of carrying out the far vision examination and the near vision examination in sequence. Alternatively, the present invention can be applied to another case where only the near vision examination is performed.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optometric apparatus comprising:
   a pair of right and left lens chamber units, each unit including a test window and optical elements to be selectively disposed in the test window; and
   a controller including a transmitting part which transmits a control signal in the form of an optical signal to the lens chamber units to selectively dispose the optical elements in the test window, the transmitting part being adapted to widen an extent of diffusion of luminous flux of the optical signal more greatly in a forward to upward directions than in a lateral direction.

2. The optometric apparatus according to claim 1, wherein the transmitting part includes a light emission part which emits the luminous flux of the optical signal and an optical element which is mounted directly ahead of the light emission part and deflects a part of the luminous flux emitted from the light emission part upward.

3. The optometric apparatus according to claim 2, wherein the optical element has a reflection face at which the part of the luminous flux emitted from the light emission part is deflected upward.

4. The optometric apparatus according to claim 3, wherein an slant angle of the reflection face is determined so that an incident angle of the luminous flux emitted from the light emission part onto the reflection face is larger than a critical angle.

5. The optometric apparatus according to claim 3, wherein an slant angle of the reflection face is determined at 45° or less with respect to a center axis of the optical element.

6. The optometric apparatus according to claim 2, wherein the optical member is rotatably mounted directly ahead of the light emission part.

7. The optometric apparatus according to claim 1, wherein each of the lens chamber units includes a lens disk holding the optical elements and a motor which rotates the lens disk, and
   the transmitting part transmits the control signal for driving the motor.

* * * * *